US012788711B2

(12) United States Patent
Kang et al.

(10) Patent No.: US 12,788,711 B2
(45) Date of Patent: Nov. 10, 2026

(54) COSMETIC COMPOSITION COMPRISING BELUGA CAVIAR EXOSOMES AS ACTIVE INGREDIENTS FOR REDUCING WRINKLES, IMPROVING MOISTURIZATION, AND IMPROVING SKIN BARRIERS

(71) Applicants: GFC LIFE SCIENCE CO., LTD., Hwaseong-si (KR); COSMAX, INC., Hwaseong-si (KR)

(72) Inventors: Hee Cheol Kang, Seoul (KR); Ji Yiung Kim, Yongin-si (KR); Hye Sung Jang, Hwaseong-si (KR); Yeo Cho Yoon, Hwaseong-si (KR); Beom Hee Ahn, Incheon (KR); Jin Woo Min, Hwaseong-si (KR); Sang Hun Han, Hwaseong-si (KR); Je Hee Han, Hwaseong-si (KR); Youn Hwa Nho, Seoul (KR); Seo Yeon Kyung, Seoul (KR); Seok Kyun Yun, Seongnam-si (KR); Seung Hyun Kang, Seoul (KR); Myeong Sam Park, Seoul (KR)

(73) Assignees: GFC LIFE SCIENCES CO., LTD., Hwaseong-si (JP); COSMAX, INC., Hwaseong-si (KR)

( * ) Notice: Subject to any disclaimer, the term of this patent is extended or adjusted under 35 U.S.C. 154(b) by 186 days.

(21) Appl. No.: 18/697,480

(22) PCT Filed: Nov. 1, 2022

(86) PCT No.: PCT/KR2022/016889

§ 371 (c)(1),
(2) Date: Mar. 31, 2024

(87) PCT Pub. No.: WO2023/080589

PCT Pub. Date: May 11, 2023

(65) Prior Publication Data

US 2024/0408002 A1 Dec. 12, 2024

(30) Foreign Application Priority Data

Nov. 4, 2021 (KR) ........................ 10-2021-0150420

(51) Int. Cl.

| | |
|---|---|
| *A61K 8/98* | (2006.01) |
| *A61K 8/14* | (2006.01) |
| *A61Q 17/00* | (2006.01) |
| *A61Q 19/00* | (2006.01) |
| *A61Q 19/08* | (2006.01) |

(52) U.S. Cl.

CPC ................ *A61K 8/987* (2013.01); *A61K 8/14* (2013.01); *A61Q 17/00* (2013.01); *A61Q 19/007* (2013.01); *A61Q 19/08* (2013.01)

(58) Field of Classification Search

None

See application file for complete search history.

(56) References Cited

U.S. PATENT DOCUMENTS

2017/0152484 A1* 6/2017 Cho ........................ A61K 8/981

FOREIGN PATENT DOCUMENTS

| | | | |
|---|---|---|---|
| KR | 20100111413 | A | 10/2010 |
| KR | 101663912 | B1 | 10/2016 |
| KR | 101964992 | B1 | 4/2019 |
| KR | 20190086280 | A | 7/2019 |
| KR | 102192317 | B1 | 12/2020 |
| KR | 20210040522 | A | 4/2021 |

* cited by examiner

*Primary Examiner* — Brian Gulledge

(74) *Attorney, Agent, or Firm* — NKL Law; Jae Youn Kim

(57) ABSTRACT

The present invention relates to a cosmetic composition for reducing wrinkles, improving moisturization, and improving skin barriers, the cosmetic composition comprising, as active ingredients, exosomes derived from Beluga caviar which are the eggs of the beluga sturgeon. The Beluga caviar exosomes provided by the present invention have excellent MMP-1 mRNA expression-inhibiting activity, COL1AL mRNA expression-increasing activity, FBN1 mRNA expression-increasing activity, HAS3 mRNA expression-increasing activity, and INV mRNA expression-increasing activity, and thus can be utilized as a cosmetic composition for reducing wrinkles, improving moisturization, and improving skin barriers.

3 Claims, 7 Drawing Sheets

Specification includes a Sequence Listing.

| | |
|---|---|
| Average size value of particles | 151.0 |
| Particle number | 1.6 x $10^{10}$/mL |

SEQUENCE LISTING

```
Sequence total quantity: 14
SEQ ID NO: 1            moltype = DNA  length = 20
FEATURE                 Location/Qualifiers
source                  1..20
                        mol_type = other DNA
                        organism = synthetic construct
SEQUENCE: 1
cgaattgccg acagagatga                                              20

SEQ ID NO: 2            moltype = DNA  length = 22
FEATURE                 Location/Qualifiers
source                  1..22
                        mol_type = other DNA
                        organism = synthetic construct
SEQUENCE: 2
gtccctgaac agcccagtac tt                                           22

SEQ ID NO: 3            moltype = DNA  length = 22
FEATURE                 Location/Qualifiers
source                  1..22
                        mol_type = other DNA
                        organism = synthetic construct
SEQUENCE: 3
tgacgttccc attagacaac tg                                           22

SEQ ID NO: 4            moltype = DNA  length = 22
FEATURE                 Location/Qualifiers
source                  1..22
                        mol_type = other DNA
                        organism = synthetic construct
SEQUENCE: 4
ccgtctttca ttacacagga ca                                           22

SEQ ID NO: 5            moltype = DNA  length = 20
FEATURE                 Location/Qualifiers
source                  1..20
                        mol_type = other DNA
                        organism = synthetic construct
SEQUENCE: 5
aatgtcagac gaagccaggg                                              20

SEQ ID NO: 6            moltype = DNA  length = 20
FEATURE                 Location/Qualifiers
source                  1..20
                        mol_type = other DNA
                        organism = synthetic construct
SEQUENCE: 6
gatttggtga cggggttcct                                              20

SEQ ID NO: 7            moltype = DNA  length = 20
FEATURE                 Location/Qualifiers
source                  1..20
                        mol_type = other DNA
                        organism = synthetic construct
SEQUENCE: 7
ggccatctct tgctcgaagt                                              20
```

-continued

```
SEQ ID NO: 8            moltype = DNA  length = 20
FEATURE                 Location/Qualifiers
source                  1..20
                        mol_type = other DNA
                        organism = synthetic construct
SEQUENCE: 8
gagaccttca acaccccagc                                              20

SEQ ID NO: 9            moltype = DNA  length = 20
FEATURE                 Location/Qualifiers
source                  1..20
                        mol_type = other DNA
                        organism = synthetic construct
SEQUENCE: 9
gtcactctgg gcatcctcat                                              20

SEQ ID NO: 10           moltype = DNA  length = 21
FEATURE                 Location/Qualifiers
source                  1..21
                        mol_type = other DNA
                        organism = synthetic construct
SEQUENCE: 10
ctattccagc acccaagaag g                                            21

SEQ ID NO: 11           moltype = DNA  length = 20
FEATURE                 Location/Qualifiers
source                  1..20
                        mol_type = other DNA
                        organism = synthetic construct
SEQUENCE: 11
tgaaacagcc aactccactg                                              20

SEQ ID NO: 12           moltype = DNA  length = 20
FEATURE                 Location/Qualifiers
source                  1..20
                        mol_type = other DNA
                        organism = synthetic construct
SEQUENCE: 12
ggagctccaa cagttgctct                                              20

SEQ ID NO: 13           moltype = DNA  length = 20
FEATURE                 Location/Qualifiers
source                  1..20
                        mol_type = other DNA
                        organism = synthetic construct
SEQUENCE: 13
ggccatctct tgctcgaagt                                              20

SEQ ID NO: 14           moltype = DNA  length = 20
FEATURE                 Location/Qualifiers
source                  1..20
                        mol_type = other DNA
                        organism = synthetic construct
SEQUENCE: 14
gagaccttca acaccccagc                                              20
```

COSMETIC COMPOSITION COMPRISING BELUGA CAVIAR EXOSOMES AS ACTIVE INGREDIENTS FOR REDUCING WRINKLES, IMPROVING MOISTURIZATION, AND IMPROVING SKIN BARRIERS

INCORPORATION OF SEQUENCE LISTING

This application contains a sequence listing submitted in Computer Readable Form (CRF). The CRF file containing the sequence listing entitled "PK3806621-Sequence-Listing.xml," which was created on Mar. 22, 2024, and is 13,330 bytes in size. The information in the sequence listing is incorporated herein by reference in its entirety.

TECHNICAL FIELD

The present disclosure relates to a cosmetic composition for reducing wrinkles, improving moisturization and skin barrier function, the cosmetic composition including exosomes derived from beluga caviar, which are large sturgeon eggs, as active ingredients.

BACKGROUND ART

Recently, skin damage caused by external factors such as fine dust, ultraviolet rays, and stress is increasing. Due to these factors, active oxygen in the skin increases, which leads to a decrease in collagen synthesis in the skin and an increase in collagen decomposition, finally resulting in the acceleration of skin aging. In addition, the function of the skin barrier protecting the human body from the external environment decreases, leading to more severe skin irritation. Due to these issues, interest in improving skin condition is increasing.

Meanwhile, beluga caviar, which are large sturgeon eggs, are known as an almost perfect food because beluga caviar are rich in protein, low in fat, and low in calories, and beluga caviar have been loved as a health food. In 1964, Ingrid Millet revealed in her study that caviar had a similar structure to human skin cells, and the benefits of caviar to skin beauty became known. That's where ingredients extracted from sturgeon eggs began to be widely used as raw materials for high-end cosmetics. Caviar are known to contain various vitamins. The contained vitamins have moisturizing, antibacterial, and sebum secretion-suppressing effects, as well as antioxidant and astringent effects. In addition, the amino acid component of caviar is a major component of the natural moisturizing factor in the epidermis, and the amino acid component is known to play an important role in preventing skin dryness and wrinkles.

Exosomes are intercellular signaling mediators that are secreted from all cells, from microorganisms to humans, and exosomes are vesicles with sizes of tens to hundreds of nanometers. The vesicles contain various substances such as various proteins, nucleic acids, and lipids, and can transfer contents therewithin by being fused with other cells. Various cell signals transmitted through vesicles regulate cell behavior, including activation, growth, migration, and differentiation of target cells. In particular, exosomes have a structure of a double phospholipid membrane similar to that of a cell membrane and are very small in size. Thus, exosomes have the advantage of not only easily penetrating the skin but also being able to easily circulate within the body and reach the inside of the skin. Representatively, exosomes isolated from stem cells are known to have effects such as wound healing, skin improvement, and wrinkle improvement without side effects. Accordingly, research on exosome components and their functions is actively underway, such as in Korean Patent Registration No. 2192317, Korean Patent Registration No. 1964992, and Korean Patent Registration No. 1663912. However, to date, there has been no research on a cosmetic composition that can simultaneously reduce wrinkles and improve moisturization and skin barrier function by using exosomes derived from beluga caviar, which are large sturgeon eggs.

Accordingly, the present inventors found that beluga caviar exosomes are excellent in inhibiting matrix metallopeptidase-1 (MMP-1) mRNA expression, increasing collagen type1 alpha 1 (COL1AL) mRNA expression, increasing fibrillin-1 (FBN1) mRNA expression, increasing hyaluronan synthase 3 (HAS3) mRNA expression, and increasing involucrin (INV) mRNA expression so that the exosomes can simultaneously reduce wrinkles and improve moisturization and skin barrier function. Based on the findings, the present inventors completed the present disclosure.

DISCLOSURE

Technical Problem

The objective of the present disclosure is to provide a composition of exosomes for reducing wrinkles and improving moisturization and skin barrier function and a method for preparing the same.

Another objective of the present disclosure is to provide cosmetics containing the composition.

Technical Solution

To achieve the objectives, the present disclosure provides a cosmetic composition for reducing wrinkles and improving moisturization and skin barrier function, the cosmetic composition including exosomes derived from beluga caviar, which are large sturgeon eggs, as active ingredients.

In the present disclosure, the exosomes derived from beluga caviar are vesicles with an average particle size in a range of 50 nm to 200 nm.

In the present disclosure, the exosomes derived from beluga caviar are contained in an amount of 0.0001% to 1% by weight based on the total weight of the composition.

Additionally, the present disclosure provides a cosmetic product containing the composition.

In addition, the present disclosure provides a method for preparing a cosmetic composition for reducing wrinkles and improving moisturization and skin barrier function, the cosmetic composition including exosomes derived from beluga caviar, which are large sturgeon eggs as active ingredients, the method including:

(a) centrifuging pulverized caviar at 2,000 to 4,000×g for 20 to 30 minutes using a centrifuge and removing the residues by taking only the supernatant;

(b) reacting the supernatant with sodium acetate and then centrifuging the resultant of the reaction at 3,000 to 5,000×g for 10 to 30 minutes for precipitation;

(c) washing the resulting precipitate with a low concentration of sodium acetate and centrifuging the precipitate at 3,000 to 5,000×g for 10 to 30 minutes to allow an exosome pellet layer to be settled; and (d) obtaining high purity exosome pellets using an ultracentrifuge after resuspending the pellet layer with distilled water.

Advantageous Effects

Beluga caviar exosomes provided by the present disclosure are excellent in inhibiting MMP-1 mRNA expression, increasing COL1AL mRNA expression, increasing FBN1 mRNA expression, increasing HAS3 mRNA expression, and increasing INV mRNA expression so that the exosomes can be used as a cosmetic composition for reducing wrinkles, improving moisturization, and improving skin barrier function.

BEST MODE

Figure 1:
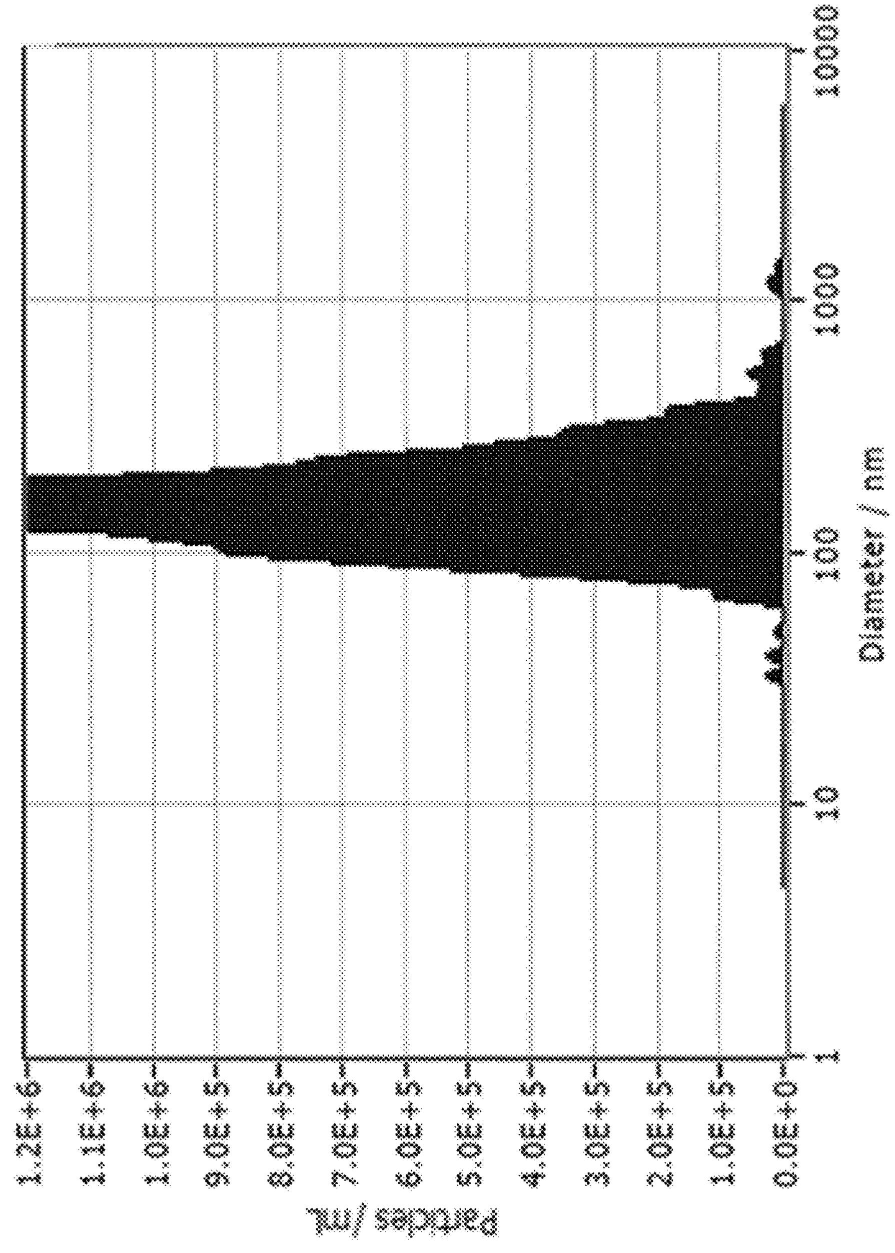
FIG. 1 is a graph showing the results of measuring the particle size distribution and particle number of beluga caviar exosomes using a particle size tracking analyzer (NTA)

Unless otherwise defined, all technical and scientific terms used in this specification have the same meaning as commonly understood by those skilled in the art to which the present disclosure pertains. In general, the nomenclature used herein is well-known and commonly used in the art.

Throughout the specification of the present application, when a part 'includes' a certain component, this means that the part may further include other components rather than excluding other components unless specifically stated to the contrary.

As terms used in the present disclosure, matrix metallopeptidase-1 (MMP-1) is abbreviated as 'MMP-1', collagen type1 alpha 1 (COL1AL) for 'COL1AL', fibrillin-1 (FBN1) for 'FBN1', hyaluronan synthase 3 (HAS3) for 'HAS3', and involucrin (INV) for 'INV'.

According to one embodiment of the present disclosure, the present disclosure is to provide a composition that is more beneficial to the skin by using exosomes, which are important substances in intercellular communication. Therefore, the present disclosure relates to a cosmetic composition for reducing wrinkles and improving moisturization and skin barrier function, the cosmetic composition including exosomes derived from beluga caviar, which are sturgeon eggs, as active ingredients.

According to another embodiment of the present disclosure, the beluga caviar-derived exosomes may be vesicles with an average particle size in a range of 50 to 200 nm. When the exosome size is within the range, the size of the vesicles is smaller than the pores, which increases the absorption ability of the exosomes into the skin, so it is preferable for the exosome size within the range in terms of improving skin elasticity.

According to yet another embodiment of the present disclosure, the exosomes derived from beluga caviar are contained in an amount of 0.0001% by weight to 1% by weight based on the total weight of the composition. When the beluga caviar-derived exosomes are contained in an amount of less than 0.0001% by weight based on the total weight of the composition, the effects of reducing wrinkles and improving moisturization and skin barrier function cannot be sufficiently obtained, and the exosome function as a composition is poor. When the beluga caviar-derived exosomes are contained in an amount of more than 1% by weight based on the total weight of the composition, it is uneconomical because sufficient efficacy can be shown even without containing more than that amount. In addition, it is undesirable because the stability and spreadability of the formulation made of the exosomes are reduced, making it difficult to use the exosomes in cosmetics.

As mentioned above, the beluga caviar-derived exosomes are excellent in inhibiting MMP-1 mRNA expression, increasing COL1A1 mRNA expression, COL1A1 being a collagen decomposition enzyme, and increasing FBN1 mRNA expression, FBN1 being a collagen synthase enzyme, so the beluga caviar-derived exosomes are effective in reducing wrinkles. In addition, the beluga caviar-derived exosomes are excellent in increasing HAS3 mRNA expression, HAS3 being a hyaluronic acid synthase enzyme, and INV mRNA expression, INV helping strengthen the skin barrier, so the beluga caviar-derived exosomes are effective in improving moisturization and skin barrier function. Therefore, the beluga caviar-derived exosomes can be used as a cosmetic composition for reducing wrinkles and improving moisturization and skin barrier function.

The cosmetic composition can be used in a variety of ways, such as cosmetics and facial cleansers for skin improvement. Products to which the composition is addable include, for example, cosmetics (for example, various creams, lotions, and skins), cleansing products, face washes, shampoos, rinses, soaps, treatments, and beauty essences.

According to yet another embodiment of the present disclosure, the present disclosure relates to cosmetics containing the composition.

In addition, the present disclosure relates to a method for preparing a cosmetic composition for reducing wrinkles and improving moisturization and skin barrier function, the cosmetic composition including exosomes derived from beluga caviar, which are large sturgeon eggs, as active ingredients, the method including:

(a) centrifuging pulverized caviar at 2,000 to 4,000×g for 20 to 30 minutes using a centrifuge and removing the residues by taking only the supernatant;

(b) reacting the supernatant with sodium acetate and then centrifuging the resultant of the reaction at 3,000 to 5,000×g for 10 to 30 minutes for precipitation;
(c) washing the resulting precipitate with a low concentration of sodium acetate and centrifuging the precipitate at 3,000 to 5,000×g for 10 to 30 minutes to allow an exosome pellet layer to be settled; and
(d) obtaining high purity exosome pellets using an ultracentrifuge after resuspending the pellet layer with distilled water.

Mode for Disclosure

Hereinafter, the present disclosure will be described in more detail through examples. These examples are solely for illustrating the present disclosure in more detail. It will be apparent to those skilled in the art that the scope of the present disclosure is not limited by these examples according to the gist of the present disclosure.

<Example 1> Preparation of Beluga Caviar-Derived Exosomes

Unsalted beluga caviar isolated from large sturgeons were used. 10 g of caviar was washed with sterilized distilled water to remove the fat portion thereof, and only pure caviar were obtained. Next, the caviar were ground in a grinder with 200 mL of new sterilized distilled water, and the caviar powder was filtered twice using a 0.7 mm mesh filter. Then, the filtered caviar powder was centrifuged at 4000×g for 20 minutes to remove grinding residues, and only the supernatant was obtained. 22 mL of 10% (pH 4.75) 1 M sodium acetate was added to the caviar powder obtained above, and the mixture was subjected to a reaction at a temperature of 4° C. for 1 hour. At this time, to induce an even reaction between the exosomes and the product from salting out, the exosomes and the product were reacted and precipitated in a shaker. After 1 hour, the exosomes and the product were still left at a temperature of 37° C. for 5 minutes to stop the reaction, and centrifuged at 5000×g for 10 minutes. After centrifugation, to wash the remaining sodium acetate, the supernatant was removed, and then 0.1 M sodium acetate was added to a precipitated pellet layer at the same pH (pH 4.75) as 1 M sodium acetate to wash the pellet layer. Centrifugation was performed again at 5000×g for 10 minutes to wash the pellet layer. After that, 100 mL of sterilized distilled water was added to the final salted-out pellet layer, and dispersion and salting-out separation were performed. Afterward, to increase the purity of the exosomes, a first centrifugation was performed at 30,000×g for 30 minutes using an ultracentrifuge. Only the supernatant was taken and ultracentrifuged again at 120,000×g for 1 hour and 30 minutes. Afterward, 100 mL of sterilized distilled water was finally added to a pellet layer, the pellet layer was dispersed, and then the beluga caviar-derived exosomes were prepared by filtration using a 0.22 um bottle-top filter.

<Comparative Example 1> Preparation of Beluga Caviar Extract

Unsalted beluga caviar isolated from large sturgeons were used. 100 g of beluga caviar was placed in 1 L of a solution containing 70% ethanol, sealed, and extracted at room temperature for 72 hours. The beluga caviar extract was vacuum-filtered with Whatman filter paper. Unfiltered contents were removed, and the remaining extract was concentrated in a rotary vacuum evaporator equipped with a cooling condenser. Afterward, the concentrated extract was suspended in 1 L distilled water and sterilized using a 0.2 um syringe filter to prepare the final beluga caviar extract.

<Experiment Example 1> Assessment of Exosome Properties

For quantitative and physical assessment of the beluga caviar-derived exosomes isolated in Example 1, an analysis was performed using a nanoparticle tracking analyzer (NTA). To measure the number and size of exosome particles, the particle size distribution and number of particles were measured using the NTA. To track the size of the exosome particles, Particle Matrix's Zetaview Zeta potential model was used. 1 mL of exosome solution was diluted in sterile distilled water at a ratio of 1/1000, the laser wavelength was set to 488 nm, and the electrical conductivity was set to 20.66 uS/cm to measure the size.

As a result, as can be seen in FIG. 1, the high purity of the beluga caviar-derived exosomes was confirmed through the SPAN value. The average particle size of exosomes was 151.0 nm, and the number of particles was $1.6\times10^{10}$ particles/mL.

<Experiment Example 2> Assessment of Cell Activity

Hs68 cells are a human fibroblast cell line, and NHEK cells are a human keratinocyte cell line. Each cell line was cultured in an incubator at a temperature of 37° C. in a 5% $CO_2$ environment using a DMEM medium containing 10% fetal bovine serum and 1% penicillin/streptomycin. The cells cultured as above were distributed in a 96-well plate at a concentration of $3\times10^3$ per well, and then the cells were cultured in an incubator at a temperature of 37° C. in a 5% $CO_2$ environment and attached to a plate for each cell line. 24 hours later, the media in the plates were replaced with media treated with each concentration of the beluga caviar-derived exosomes of Example 1 and the beluga caviar extract of Comparative Example 1, the cells in each plate were cultured, and then the media of the plates were removed 48 hours later. 10% WST-1 reagent was applied to each well. After the cells' reactions with the reagent in an incubator for 2 hours, the absorbance value was measured at a wavelength of 450 nm using an ELISA reader, and then the cell viability was measured according to the following [Equation 1].

$$\text{Cell viability (\%)}=(\text{absorbance of test substance})/\text{absorbance of control group}) \quad \text{[Equation 1]}$$

Figure 2:
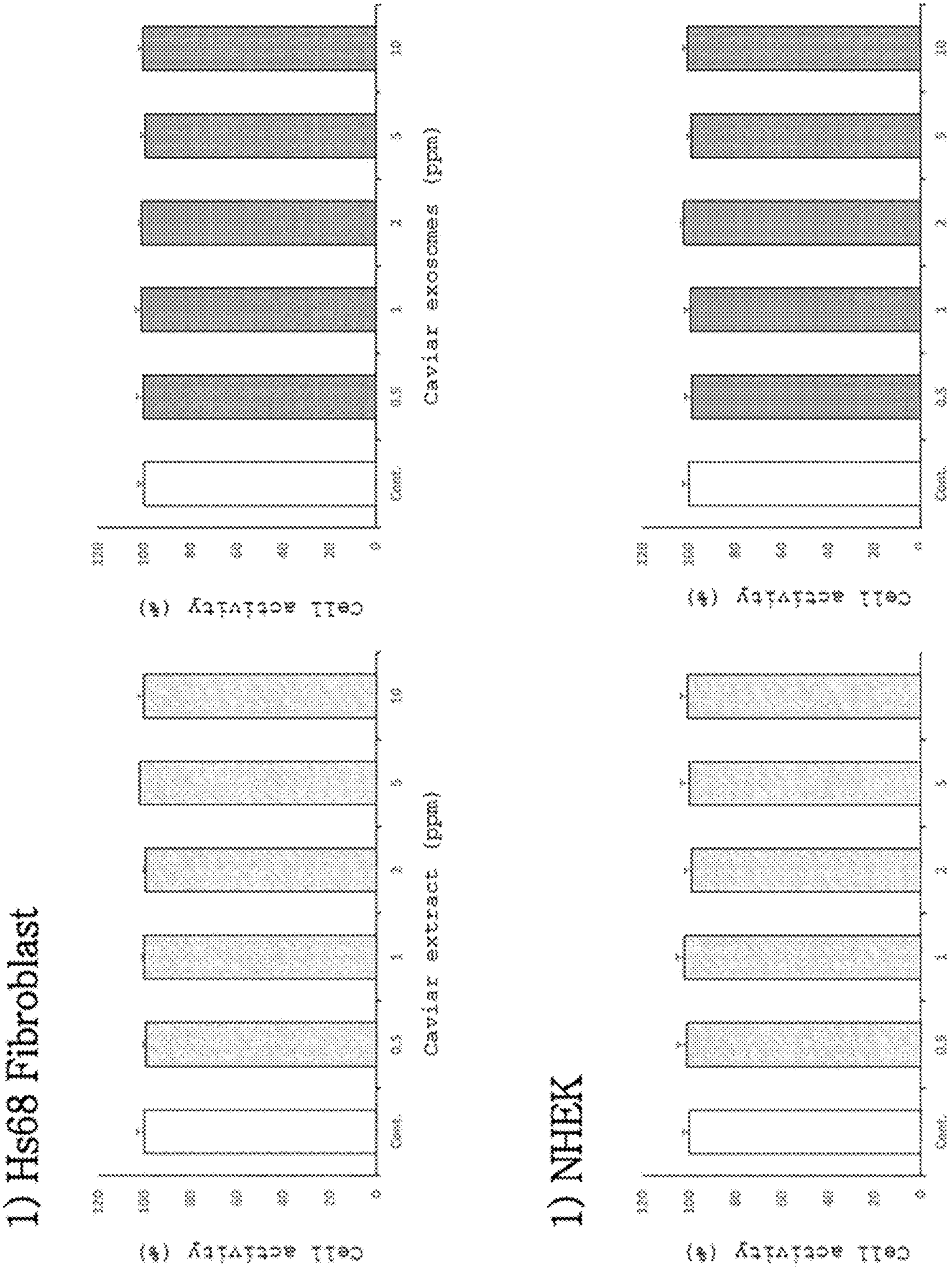
FIG. 2 is a diagram showing the results of confirming cell activity in human fibroblasts and human keratinocytes when each of the beluga caviar exosomes according to the present disclosure and the caviar extracts as a comparison group was applied to human fibroblasts and human keratinocytes, respectively.

As a result, as can be seen in FIG. 2, due to the effects of Example 1 and Comparative Example 1, the survival rate of Hs68 cells (human fibroblasts) and NHEK cells (human keratinocytes) was over 90%, showing low toxicity.

<Experiment Example 3> Anti-Wrinkle Efficacy Test: Measurement of MMP-1, COL1A1, and FBN1 mRNA Expression Levels To determine the effect of the beluga caviar-derived exosomes of Example 1 and the beluga caviar extract of Comparative Example 1 on reducing skin wrinkles, MMP-1, COL1A1, and FBN1 mRNA expression levels were measured. Hs68 cells (human fibroblast cell line) were seeded into a 6-well plate in an amount of $4\times10^5$ and cultured in an incubator at a temperature of 37° C. and 5% $CO_2$ conditions for 24 hours. Afterward, in the case of the experimental group subject to measurement of MMP-1 mRNA expression level, the medium was removed, and DPBS was added. The remaining cell groups, excluding the UVB ray non-irradiated group, were irradiated with 20 mJ/$cm^2$ of UVB ray. The experimental group subject to measurement of COL1A1 and FBN1 mRNA expression levels was not irradiated with a UV ray. Next, the cells were treated and reacted with the beluga caviar-derived exosomes of Example 1 and the beluga caviar extract of Comparative Example 1 each with a concentration of 1 ppm. Afterward, RNAs were isolated from the cells treated with each sample using Trizol (RNA iso, TAKARA, Japan). The RNAs were quantified at a wavelength of 260 nm using a nanodrop. cDNAs were synthesized in an amplifier using 2 ug of RNA each (C1000 Thermal Cycler, Bio-Rad, USA). A real-time polymerase chain reaction was performed in a real-time PCR machine using a mixture of the synthesized cDNAs with target gene-specific primers and a cyanine dye, which was SYBR Green supermis (Applied Biosystems, USA). Through the process, the expression level of the target genes was finally assessed. The primer sequences and reaction conditions are shown in Table 1 below, and the expression level of the genes was finally analyzed through correction for the β-actin gene.

TABLE 1

| Sequence number | Gene | Primer direction | Sequence (5'→3') | Reaction conditions |
|---|---|---|---|---|
| 1 | MMP-1 | F | 5'-CGAATTGCCGACAGAGATGA-3' | Polymerization reaction in 40 cycles under conditions of 95° C. for 15 seconds, 58° C. for 30 seconds, and 72° C. for 30 seconds after polymerase activation at 95° C. for 10 minutes |
| 2 | | R | 5'-GTCCCTGAACAGCCCAGTACTT-3' | |
| 3 | COL1A1 | F | 5'-TGACGTTCCCATTAGACAACTG-3' | |
| 4 | | R | 5'-CCGTCTTTCATTACACAGGACA-3' | |
| 5 | FBN1 | F | 5'-AATGTCAGACGAAGCCAGGG-3' | |
| 6 | | R | 5'-GATTTGGTGACGGGGTTCCT-3' | |
| 7 | β-Actin | F | 5'-GGCCATCTCTTGCTCGAAGT-3' | |
| 8 | | R | 5'-GAGACCTTCAACACCCCAGC-3' | |

Figure 3:
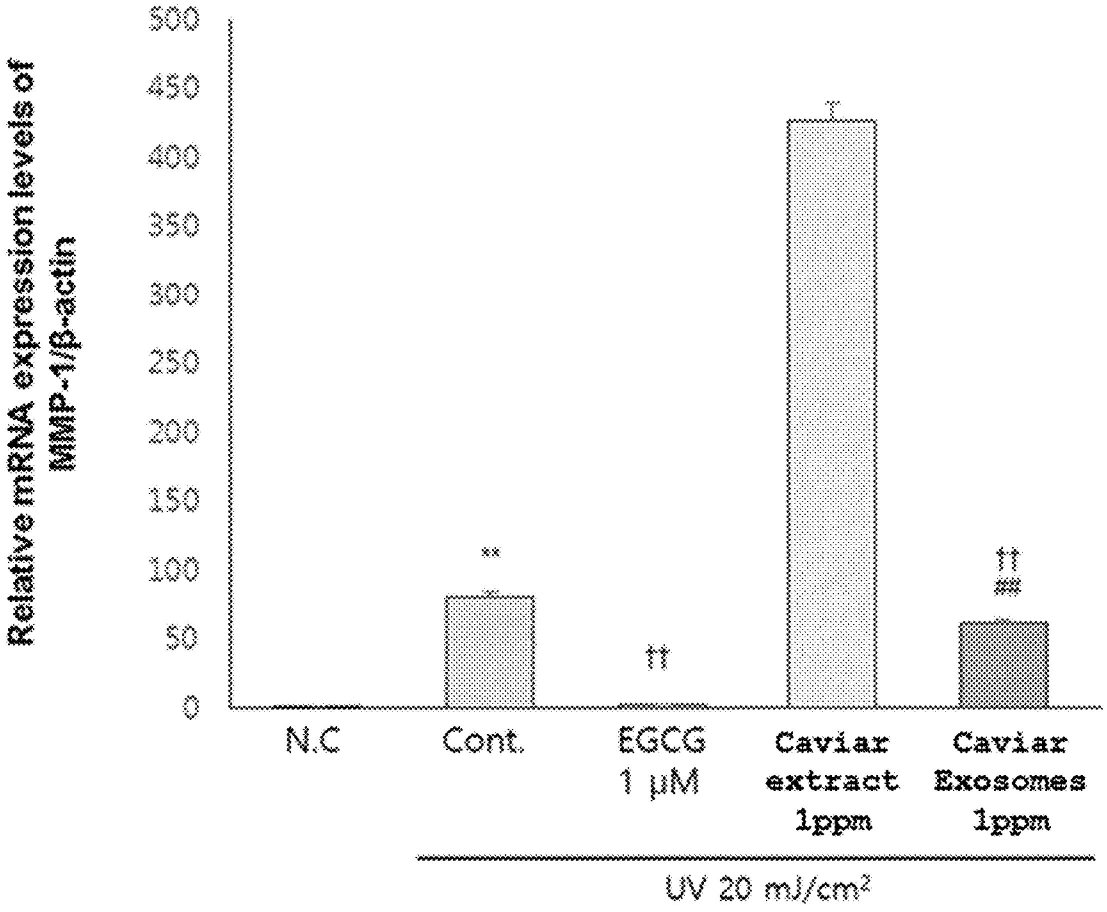
FIG. 3 is a diagram showing the results of confirming the effect of beluga caviar exosomes and caviar extracts on reducing MMP-1 factor expression in human fibroblasts when each of the beluga caviar exosomes according to the present disclosure and the caviar extracts as a comparison group were applied.

As a result, as can be seen in FIG. 3, it was confirmed that the beluga caviar-derived exosomes of Example 1 reduced MMP-1 mRNA expression compared to the control group. In addition, it was confirmed that the effect of the beluga caviar-derived exosomes of Example 1 on reducing MMP-1 mRNA expression was significantly superior to that of the beluga caviar extract of Comparative Example 1.

Figure 4:
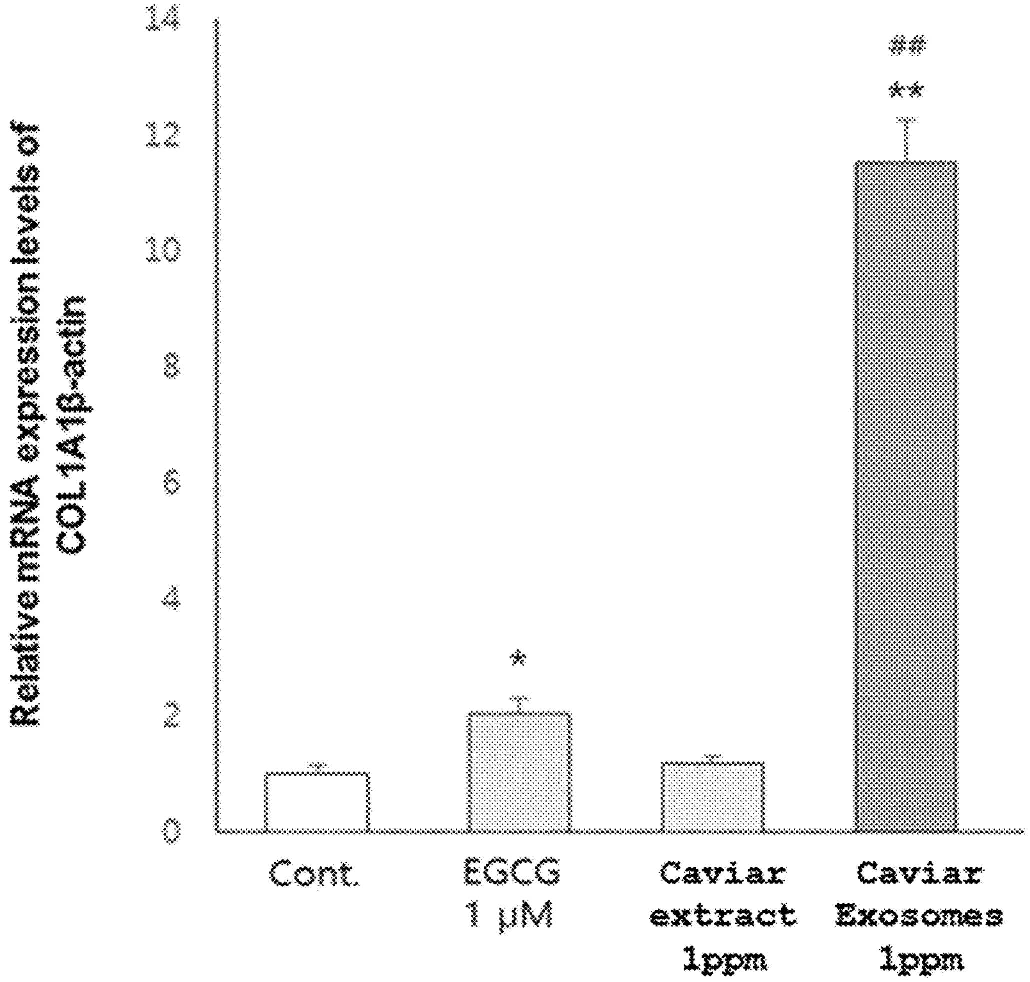
FIG. 4 is a diagram showing the results of confirming the effect of beluga caviar exosomes and caviar extracts on increasing COL1A1 factor expression in human fibroblasts when each of the beluga caviar exosomes according to the present disclosure and the caviar extracts as a comparison group were applied.
Figure 5:
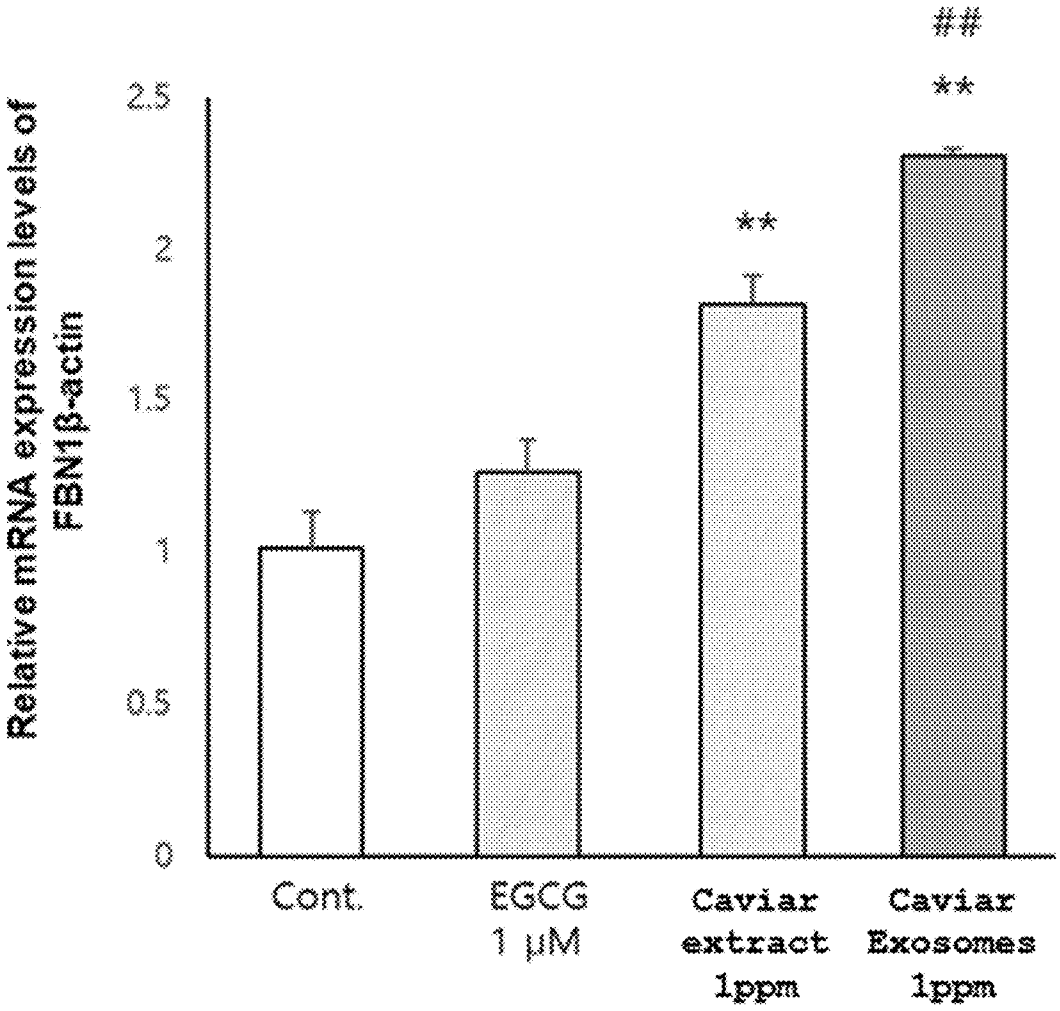
FIG. 5 is a diagram showing the results of confirming the effect of beluga caviar exosomes and caviar extracts on increasing FBN-1 factor expression in human fibroblasts when each of the beluga caviar exosomes according to the present disclosure and the caviar extracts as a comparison group were applied.

Additionally, as can be seen in FIGS. 4 and 5, it was confirmed that the beluga caviar-derived exosomes of Example 1 increased CCOL1A1 mRNA and FBN1 mRNA expression. In addition, it was confirmed that the effect of the beluga caviar-derived exosomes of Example 1 on increasing CCOL1A1 mRNA and FBN1 mRNA expression was superior to that of the beluga caviar extract of Comparative Example 1.

Therefore, it was confirmed that exosomes derived from beluga caviar, which are large sturgeon eggs, were effective in reducing skin wrinkles by reducing MMP-1 mRNA expression and increasing CCOL1A1 mRNA and FBN1 mRNA expression.

<Experiment Example 4> Measurement of HAS3 and INV mRNA Expression Levels

To determine the effects of the beluga caviar-derived exosomes of Example 1 and the beluga caviar extract of Comparative Example 1 on improving skin moisturization and strengthening skin barrier, HAS3 and INV mRNA expression levels were measured and assessed. HaCaT cells (keratinocytes) were seeded into a 6-well plate in an amount of $5\times10^5$ and cultured in an incubator at a temperature of 37° C. and 5% $CO_2$ conditions for 24 hours. Next, the cells were treated and reacted with the beluga caviar-derived exosomes of Example 1 and the beluga caviar extract of Comparative Example 1 each with a concentration of 10 ppm. Afterward, RNAs were isolated from the cells treated with each sample using Trizol (RNA iso, TAKARA, Japan). The RNAs were quantified at a wavelength of 260 nm using a nanodrop. cDNAs were synthesized in an amplifier using 2 ug of RNA each (C1000 Thermal Cycler, Bio-Rad, USA). A real-time polymerase chain reaction was performed in a real-time PCR machine using a mixture of the synthesized cDNAs with target gene-specific primers and a cyanine dye, which was SYBR Green supermis (Applied Biosystems, USA). Through the process, the expression level of the target genes was finally assessed. The primer sequences and reaction conditions are shown in Table 2 below, and the expression level of the genes was finally analyzed through correction for the β-actin gene.

TABLE 2

| Sequence number | Gene | Primer direction | Sequence (5'→3') | Reaction conditions |
|---|---|---|---|---|
| 9 | HAS3 | F | 5'-GTCACTCTGGGCATCCTCAT-3' | Polymerization reaction in 40 cycles under conditions of 95° C. for 15 seconds, 58° C. for 30 seconds, and 72° C. for 30 seconds after polymerase activation at 95° C. for 10 minutes |
| 10 | | R | 5'-CTATTCCAGCACCCAAGAAGG-3' | |
| 11 | INV | F | 5'-TGAAACAGCCAACTCCACTG-3' | |
| 12 | | R | 5'-GGAGCTCCAACAGTTGCTCT-3' | |
| 13 | β-Actin | F | 5'-GGCCATCTCTTGCTCGAAGT-3' | |
| 14 | | R | 5'-GAGACCTTCAACACCCCAGC-3' | |

Figure 6:
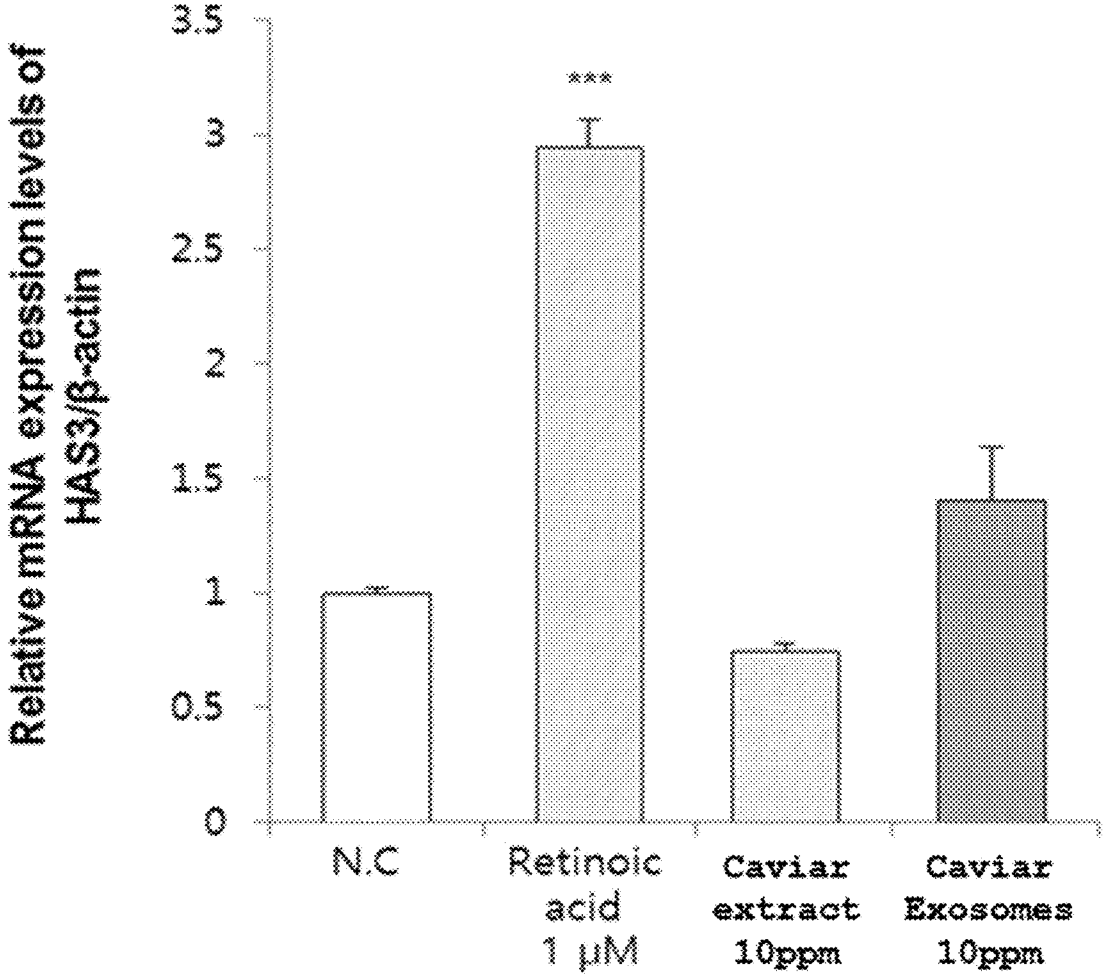
FIG. 6 is a diagram showing the results of confirming the effect of beluga caviar exosomes and caviar extracts on increasing HAS3 factor expression in human keratinocytes when each of the beluga caviar exosomes according to the present disclosure and the caviar extracts as a comparison group were applied.
Figure 7:
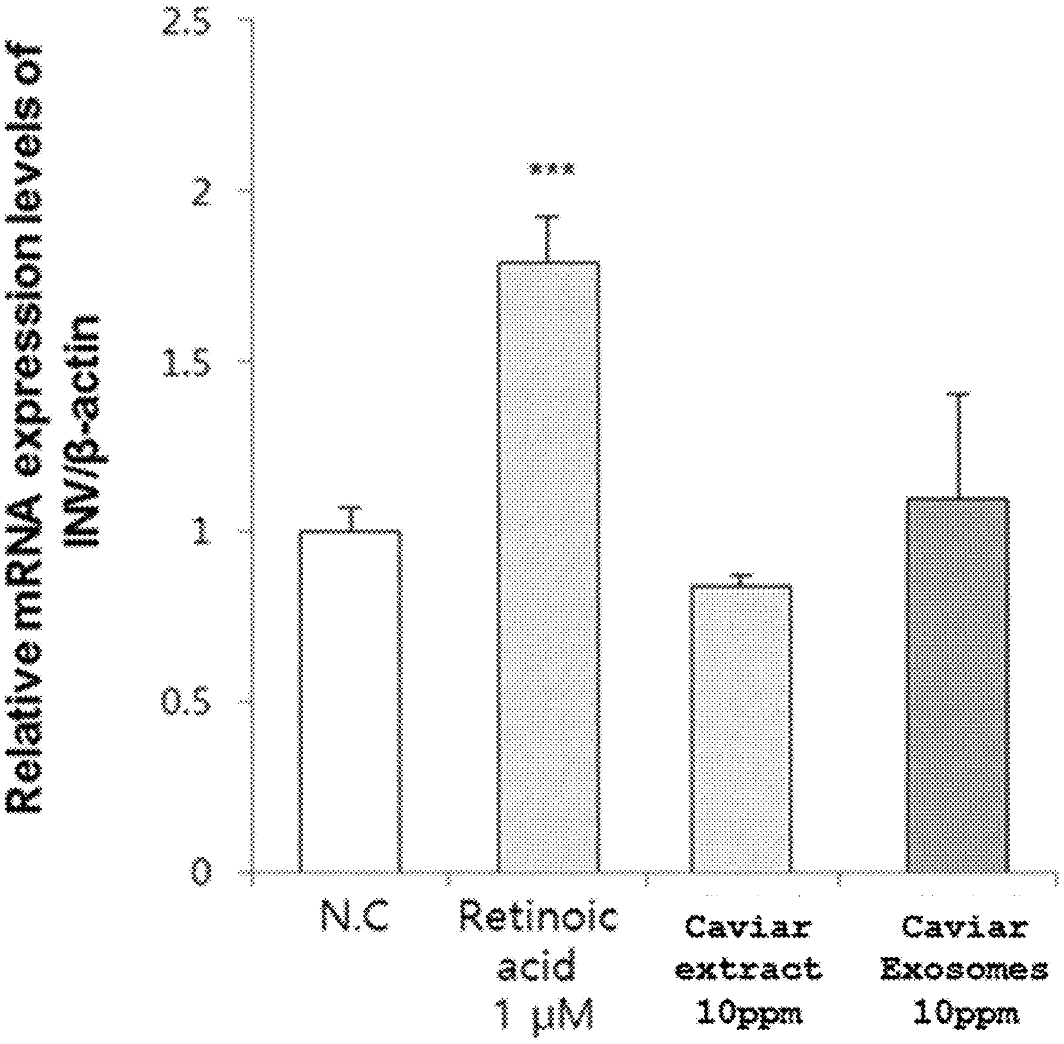
FIG. 7 is a diagram showing the results of confirming the effect of beluga caviar exosomes and caviar extracts on increasing INV factor expression in human keratinocytes when each of the beluga caviar exosomes according to the present disclosure and the caviar extracts as a comparison group were applied.

As a result, as can be seen in FIGS. 6 and 7, it was confirmed that the beluga caviar-derived exosomes of Example 1 increased HAS3 mRNA and INV mRNA expression. In addition, it was confirmed that the effect of the beluga caviar-derived exosomes of Example 1 on increasing HAS3 mRNA and INV mRNA expression was significantly superior to that of the beluga caviar extract of Comparative Example 1.

Therefore, exosomes derived from beluga caviar, which are large sturgeon eggs, were excellent in improving moisturization and strengthening skin barrier by increasing HAS3 mRNA and INV mRNA expression.

Consequently, the exosomes of beluga caviar, which are large sturgeon eggs, and being provided by the present disclosure were excellent in inhibiting MMP-1 mRNA expression, increasing COL1AL mRNA expression, increasing FBN1 mRNA expression, increasing HAS3 mRNA expression, and increasing INV mRNA expression so that the exosomes had the effects in improving moisturization and skin barrier function.

Herein above, specific parts of the present disclosure have been described in detail. It will be apparent to those skilled in the art that these techniques only have differences and do not limit the scope of the disclosure. Accordingly, the substantial scope of the present disclosure will be defined by the appended claims and their equivalents.

INDUSTRIAL APPLICABILITY

Beluga caviar exosomes provided by the present disclosure are excellent in reducing wrinkles and improving moisturization and skin barrier function, so the exosomes can be used as a cosmetic composition for reducing wrinkles and improving moisturization and skin barrier function. The exosomes can be usefully applied to cosmetics for skin improvement that contain the exosomes as active ingredients.

The invention claimed is:

1. A method for a skin condition for reducing wrinkles, improving moisturization, or strengthening skin barrier function, the method comprising applying to a subject in need thereof a cosmetic composition comprising exosomes derived from beluga caviar being large sturgeon eggs as an active ingredient.

2. The method of claim 1, wherein the exosomes derived from beluga caviar are vesicles with an average particle size in a range of 50 to 200 nm.

3. The method of claim 1, wherein the exosomes derived from beluga caviar are contained in an amount of 0.0001% to 1% by weight based on the total weight of the composition.

* * * * *